United States Patent [19]

Law et al.

[11] Patent Number: 4,685,620

[45] Date of Patent: Aug. 11, 1987

[54] LOW-VOLUME ELECTROSTATIC SPRAYING

[75] Inventors: S. Edward Law, Athens, Ga.; Henry D. Bowen, Raleigh, N.C.

[73] Assignees: The University of Georgia Research Foundation Inc., Athens, Ga.; North Carolina State University, Raleigh, N.C.

[21] Appl. No.: 781,487

[22] Filed: Sep. 30, 1985

[51] Int. Cl.$^4$ .................. B05D 1/06; A01N 25/08; A01N 25/06

[52] U.S. Cl. .................................. 239/3; 427/4; 427/27

[58] Field of Search .................. 239/3; 427/4, 25, 26, 427/27

[56] References Cited

U.S. PATENT DOCUMENTS 4,168,327 9/1979 Law .................................. 427/4
4,565,318 1/1986 Inculet ............................. 239/3

Primary Examiner—Evan K. Lawrence
Attorney, Agent, or Firm—Oblon, Fisher, Spivak, McClelland & Maier

[57] ABSTRACT

A method for increasing the efficiency of electrostatic deposition of particulate matter on a surface, which comprises preparing a dispersion of electrostatically charged particles of an active material to be deposited on the surface, wherein the particles of active material have an average radius of $r_{p1}$ and a total volume of $V_{L1}$, in a space adjacent to the surface which contains a dispersion of particles of an inert material, electrostatically charged with the same polarity as said particles of active material, wherein the particles of inert material have an average radius of $r_{p2}$ and a total volume of $V_{L2}$, wherein $r_{p1} > r_{p2}$ and $$\frac{V_{L2}}{V_{L1}} \geq 0.2.$$

11 Claims, 8 Drawing Figures

FIG. 8

LOW-VOLUME ELECTROSTATIC SPRAYING

BACKGROUND OF THE INVENTION

1. Field of the Invention:

This invention relates to electrostatic spraying of active materials onto surfaces and is particularly related to low volume applications.

2. Discussion of the Background:

Low-volume electrostatic spraying has been used from time to time in agriculture to spray pesticides on crops. Additionally, electrostatic coating operations are routinely used industrially to coat an active material, such as a paint or a doping agent, on a surface. In general, electrostatic coating of surfaces involves forming the coating material into finally divided particles or droplets, charging the particles or droplets to a single polarity (e.g., negative) and the surface to be coated to a different polarity (e.g., positive). Even at the ground potential (E=0), the coating target surface has induced into it from the "ground reservoir" a very appreciable net charge of sign opposite to the incoming charge cloud of coating particles. As a result of electrostatic attraction and the proximity of the particles or droplets to the surface to be coated, electrostatic forces move the particles toward the surface where they are deposited to form a coat or layer. Various prior art electrostatic coating applications are more sophisticated modifications of this simple situation. They differ from one another in the manner in which the particles are formed, the means by which they are charged, the particular aspects of the methods by which the particles are distributed about the surface, and the manner in which the particles collect on the surface. A review of prior art electrostatic processes can be found in Moore, A. D., Ed., *Electrostatics and its Applications*, Wiley and Sons, 1973, particularly pages 250-280.

The use of electrostatic spraying or coating is widespread in controlled industrial environments where low-volume painting and other coating operations are generally conducted. Electrical hazards due to high voltages that are typically used are minimized in such controlled industrial environments. However, electrostatic spraying has recently been made available to agricultural spraying operations through the use of electrostatic spray nozzle systems using shielded voltage sources. Examples of agriculture applications are set forth in numerous United States patents, of which the following are examples.

Law, U.S. Pat. No. 4,004,733, discloses an electrostatic spray nozzle system using a low voltage power supply that is particularly designed for agriculture applications. Law, U.S. Pat. No. 4,168,327 describes a method for controlling the space-charge density of the spraying operation in order to produce an optimal deposition level. Malcolm, U.S. Pat. No. 4,328,940, describes a method of spraying electrically charged particulate materials to ground from a low flying airplane. The method includes the steps of imposing an electrical charge of a given polarity upon an emitted primary spray of particulate material while concurrently emitting a secondary spray of oppositely charged particulate material to avoid production of an opposite charge on the aircraft during the spraying operation. DeVittorio, U.S. Pat. No. 4,341,347, discloses a nozzle capable of imposing a high electrostatic charge on very small particles in order to improve their spray characteristics. All of these patents disclose various low volume spraying operations.

Nevertheless, their remains a need for methods of electrostatic spraying which utilize even lower volumes of liquids and which produce less waste than is now obtainable with current methods.

SUMMARY OF THE INVENTION

Accordingly, one obejct of this invention is to provide a novel method for depositing particulate matter on a surface having an increased efficiency of deposition, thereby reducing the volume of the coating material used and eliminating waste or harmful environmental effects.

This and other objects of the invention as will hereinafter become more readily apparent have been accomplished by providing a method for increasing the efficiency of deposition of particulate matter on a surface, which comprises preparing a dispersion of electrostatically charged particles of an active material to be deposited on the surface, wherein the particles of active material have an average radius of $r_{p1}$ and a total volume of $V_{L1}$, in a space adjacent the surface which contains a dispersion of particles of an inert material electrostatically charged with the same polarity as the particles of active material, wherein the particles of inert material have an average radius of $r_{p2}$ and a total volume of $V_{L2}$, wherein $r_{p1}$ is greater than $r_{p2}$ and $$\frac{V_{L2}}{V_{L1}} \geq 0.2.$$

This method is particularly useful in agricultural applications but is also useful in any other process (such as spray painting) in which a particulate matter is being deposited on the surface.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 8 is a graph showing the enhancement of toxic particle terminal velocity due to the presence of an inert spray of various sizes.

DESCRIPTION OF THE PREFERRED EMBODIMENTS

Figure 1:
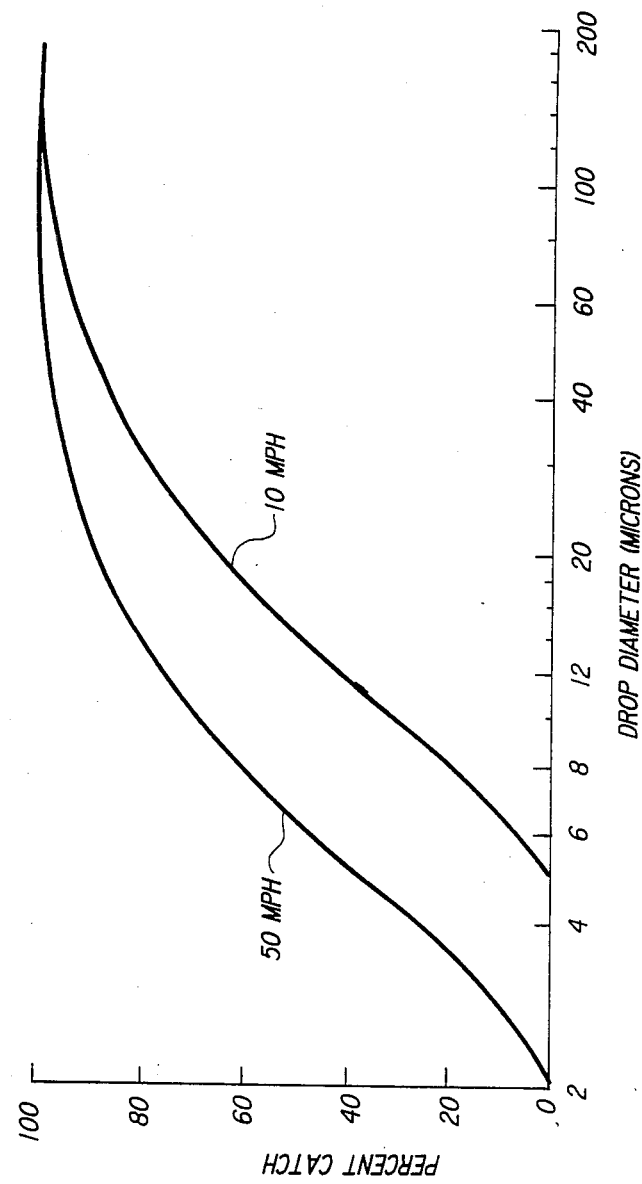
FIG. 1 is a graph showing the percentage catch of particles on a surface versus drop diameter of the particles.

The present invention is a method of electrostatic spraying which inreases the efficiency of deposition of active materials, such as paints or pesticides, on target surfaces. The method comprises using relatively small charged particles of an inert or non-toxic material to produce an electrical field in the space where the spraying operation is being conducted. This electric field drives the larger charged particles of the active material onto the target surface. For example, with a mixture of particles that is 50% by weight (volume) of 1 micrometer particles and 50% by weight (volume) of 50 micrometer particles, essentially all of the larger particles can be deposited on targets, such as plant parts or metal surfaces, by virtue of differential migration velocities of the particles.

The concept rests in part on the following basic facts: (1) the terminal velocity of particles in a uniform electric field of strength E is proportional to the effective radius of the particle if all particles of all sizes are charged in the same manner (2) for a given weight of material the number of particles increases as the cube of the radius; (3) the electric charge carried by particles is proportional to the surface area of the particles. These three results of the laws of physics allow the dual particle concept to operate successfully.

Terminal velocity is an important concept in understanding the present invention. Terminal velocity is the final speed of a small particle falling in air. As the particle begins to accelerate its initial falling speed is zero. Several seconds are required before the rate of fall ceases to increase due to air resistance. When the particle reaches its maximum speed of fall, it has reached its terminal velocity. We are all familiar with the idea that small particles of clay fall more slowly than coarse particles of sand when both are mixed in a glass of water and acted upon by the steady force of gravity. Small particles fall through air in the same manner, and the terminal velocity due to weight of the particle can be calculated. By the same token a particle has a terminal velocity (final speed) when in a uniform electric field. Thus two particles in the same electric field strength move at different rates. The larger the particle the faster it moves toward an electrically grounded object. As an example, if the ratio of the radius and diameter of one of two particles is 10 times that of the other and both passed through the same charging nozzle (or are otherwise charged in the same manner) the larger particle would speed toward the target plant at 10 times the speed of the smaller particle. This means that all of the larger particles can on the average be deposited in the same time that only 10% of the small particles have deposited. This has the advantage that 90% of the small particles are still in the air providing a considerable electric field to drive the larger toxic (or otherwise active) particles that are being deposited. With 50% of the powder mixture composed of 1 micron diameter particles and 50% composed of 10 micron diameter particles the total electric field available for driving the charged particles onto the plant is about 90% carried by the smaller particles of the mixture and only 10% is carried by the larger particles since the number of 1 micron particles is much larger than the number of 10 micron particles.

The dual particle concept is readily implemented on a practical basis. Ideally the active ingredients should be 5 to 25 times as large as the inactive ingredients to obtain the maximum benefits from the dual particle system. From a practical point of view any ratio of particle sizes greater than 1 favors the dual particle concept compared to a mono size or a broad spectrum of particle sizes. Standard micromizing mills operated with air or steam can grind dust particles to ½ to 3 microns. Two fluid pneumatic sprayer nozzles can be adjusted to give particles in the 10 to 50 micron range which has been found to be the most effective size particle sizes for most insect and disease control purposes. If the toxic and diluent particles are both powders then they can be mixed at the factory and passed through the same ionized field charging nozzle of which there are many versions available.

If the diluent is a powder or oil smoke and the active ingredient is a spray then the ingredients may be mixed by blowing the two charged streams into the same space simultaneously or sequentially. They can be mixed by two or more impinging jets having their particles charged to the same electrical sign (either positive or negative).

Powder agglomerating disks and drums are standard equipment used for making larger particles from smaller particles. If the two particle streams are both sprays it is only a matter of impinging two separate streams charged to the same electrical sign either parallel or at an angle to each other. These two streams of charged particles will mix best and most thoroughly by impinging streams at an angle that causes a great deal of turbulence. The common electrical sign of the particles keeps them from coalescing.

The diluent (inert) particles in many cases are mixed with toxic pesticide particles in order to get sufficient volume for accurate metering of powders. Thus a diluent is preferred. For sprays the diluent or small particles necessary for the benefits of the dual particle scheme need be nothing more than water or an oil carrier. In that case pneumatic nozzles or ultrasonic nozzles are used for producing the very small droplets while the same equipment using a second nozzle will produce the larger particles.

The invention can be practiced with very simple equipment. For example a 20-year old device that has found great favor for fast application of powdered diluent and active ingredient pesticide applications in Japan comprises a polyethylene pipe that supports itself by the air jets that come out of the bottom of the pipe. Two men can operate a duster of this type with a tube that is from 5 to 150 meters (550 feet) and can cover a very large acreage in a very short time with relatively inexpensive equipment. However, with present equipment the amount of chemical dispensed is still 4 to 10 times that remaining on the plant. Application rates of toxic and the resulting pollution to air and water materials from runoff is on the order of 4 to 20 times what it would be if the proper mix of particles and charging nozzles were put on the devices. The present invention provides significant long term benefits by reducing the amount of chemical applied that is normally lost to the environment.

It is technically possible to put every toxic pesticide particle on the target plant using the dual particle concept, while it is not possible to consistently get more than 60 to 70% of the toxic particles deposited onto the target plant even by standard electrostatic methods. By taking advantage of the dual particle principle in designing the equipment and formulations of powder and spray used for insecticides, plant and animal pathogens, and non-systemic herbicides, even greater improvements may be made in the future.

Additional methods of applying dust and powders are well known and can readily be adapted to the practice of this invention. For example, dusting equipment that can be converted to electrostatic dusting has been available for some twenty years as described in *Farming Japan*, Volume 2, August 1968, pages 51–54 and Fujiki, *Agricultural Bulletin of Saga University*, 37:1–89 (1974). The latter reference describes studies on predicting pressure distribution and designing perforations of dust heads for use in dusting operations.

It is not necessary that discrete ranges of particle sizes be used in order to practice the present invention. It is merely necessary that the inert driving particles be smaller on average than the active component particles. The greater the difference in size, the greater the driving force will be. There is generally an upper limit of approximately 50 microns for heavy particles (such as metal particles) for use in electrostatic spraying. Larger particles are generally so heavy as to result in a greater influence of gravity and a lessening of the influence of electrostatic forces. Limits on the large active particles of 25–50 microns generally give excellent results. The small inert particles are preferred to be 5 microns or less in diameter. Either smoke or water can preferably be used to produce these small particles. Water can be used even in combination with dry dust since the electrostatic charges present tend to keep the particles separated from each other. Accordingly, it is possible to practice this invention with any combination of wet and dry/large and small particles.

The method of the present invention provides a means for applying pesticides to the undersides of leaves and to other surfaces that do not have a direct line of sight to the spraying nozzle. Neither conventional spraying or normal electrostatic spraying is able to achieve this result with the degree of efficiency obtained.

A preferred technique for practicing the present invention involves the use of two jets fixed at an angle to spray into the same space so as to mix the particles of different sizes. In agricultural operations, it is particularly desirable to operate the jet of small particles within the leaves of the plant (for example, by operating the jet at a height below the top of the plants) in order to obtain a uniform space charge that will drive the larger active particles to all parts of the plant being treated.

As demonstrated in the theoretical mathematical calculations set forth below that can be used for guidance in designing specific systems to carry out the invention other than those specifically described herein, the migration velocities in any specified electric field are linearly proportional to particle diameter. Since the charge on a particle is proportional to its surface area, individual 50 micrometer particles have 2500 times the charge of an individual 1 micrometer particle which is charged in the same charging nozzle. However, in a 50-50 mixture by weight, there are 124,000 times as many small particles, so that only about 2% of the charge is being carried by the large particles. When the large particles (with high migratory velocities) interact with the charged carried primarily by the small particles (of low migratory velocities), the large particles are rapidly driven to the target with only a minimal depletion of the electric field.

The use of this process is expected to reduce the required application rates of active materials to from $\frac{1}{3}$ to $\frac{1}{8}$ of the rates currently used. Furthermore, in agricultural spraying applications, the method makes it possible to formulate the toxic agricultural formations to their most effective size while still applying most of the toxic particles to the target plant and reducing drift to non-target plants or other parts of the environment. In pesticide applications, relatively small amounts of a non-toxic (inert) non-evaporating material, such as a smoke, oil mist, or dust particle, are effective in driving larger-sized toxic materials to the plant target. Essentially all of the larger particles are filtered out and deposited on plants such as cotton, soybeans, peanuts, grasses, vegetables, and trees. Since the small particles used are inert, problems caused by pesticide drift (which are greater for small particles) are virtually eliminated.

As will become clear from the mathematical model described later, the higher the ratio of the small particles to larger particles by weight, the greater the efficiency of collection of the larger particles by the surface on which deposition is desired. However, the weight ratio of the small particles to large particles in a mixture of small and larger particles may be varied over a wide range while substantial benefits are still obtained. In fact, positive results are obtained even when the amount of inert material is less than that of the active material. Furthermore, the larger the difference in size of the larger and small particles, the greater the efficiency of removal of the large particles. Nevertheless, this ratio can also be varied as long as there is a difference in size between the inert and active materials (the active material being present in a larger average size).

It is not necessary to fully mix the particles in order to achieve the benefits described above. The large particles can be discharged from a different source from the small particles and injected into the small particle, air, or gas stream. Likewise, the charging level of the two sizes of particles can be different to obtain different deposit characteristics.

The method of the invention is not limited to applying pesticides but is also applicable to a number of other agricultural and non-agricultural applications including, but not limited to, removal of undesirable and/or toxic materials from air or other gas streams, spray painting and other types of industrial coating operations, and weather modifications such as cloud seeding.

When the present invention is applied to agricultural spraying, it is possible to achieve significant economic benefits even over those normally obtained with ultra-low volume (ULV) application techinques. The present method solves many of the problems of proper spatial coverage of plant surfaces by deposited pesticide droplets that are not translocated by biological processes within the plant. There is a lower limit on the number of droplets which must be deposited per unit leaf area if the active material is not translocated. For ULV rates, this contraint dictates that droplet diameter must decrease as compared with the droplet sizes used in high-ergallonage conventional spraying. However, both theoretical and experimental results indicate that several physical phenomena have opposing effects upon the desired biological test control as droplet size is reduced.

Various investigators have shown that the biological effectiveness of pesticide spray increases as droplet size decreases. Ennis and Williamson (6) showed increases in yield inhibition caused by herbicidal sprays on several test crops as droplet size decreased. Himel's work (7,8,9) indicates that droplets smaller than 50 microns diameter are mainly the ones which provide insect control. Field tests utilizing a fluorescent tracer technique for the study of over 100,000 droplets actually found deposited on target insects, indicate that more than 98% of these deposited droplets were in the range of 20 microns diameter (9). No traces of droplets larger than 114 microns were found on any insects examined. Similar tests utilizing laser holography for observation of droplets deposited upon insects substantiate these findings by Himel (12).

In addition to the above desirable factors associated with small droplet size, there are also problems caused by the reduced capability to deposit these small particles upon target surfaces. FIG. 1 illustrates the effect which a particle's linear momentum has upon its probability to impinge upon a deposit surface (3). Percent catch is seen to decrease rapidly with a decrease in droplet diameter, and this introduces severe problems into the ULV technique. Also, Threadgill and Smith (13) and others have verified the increased drift potential of airborne droplets in the ULV size range.

Figure 2:
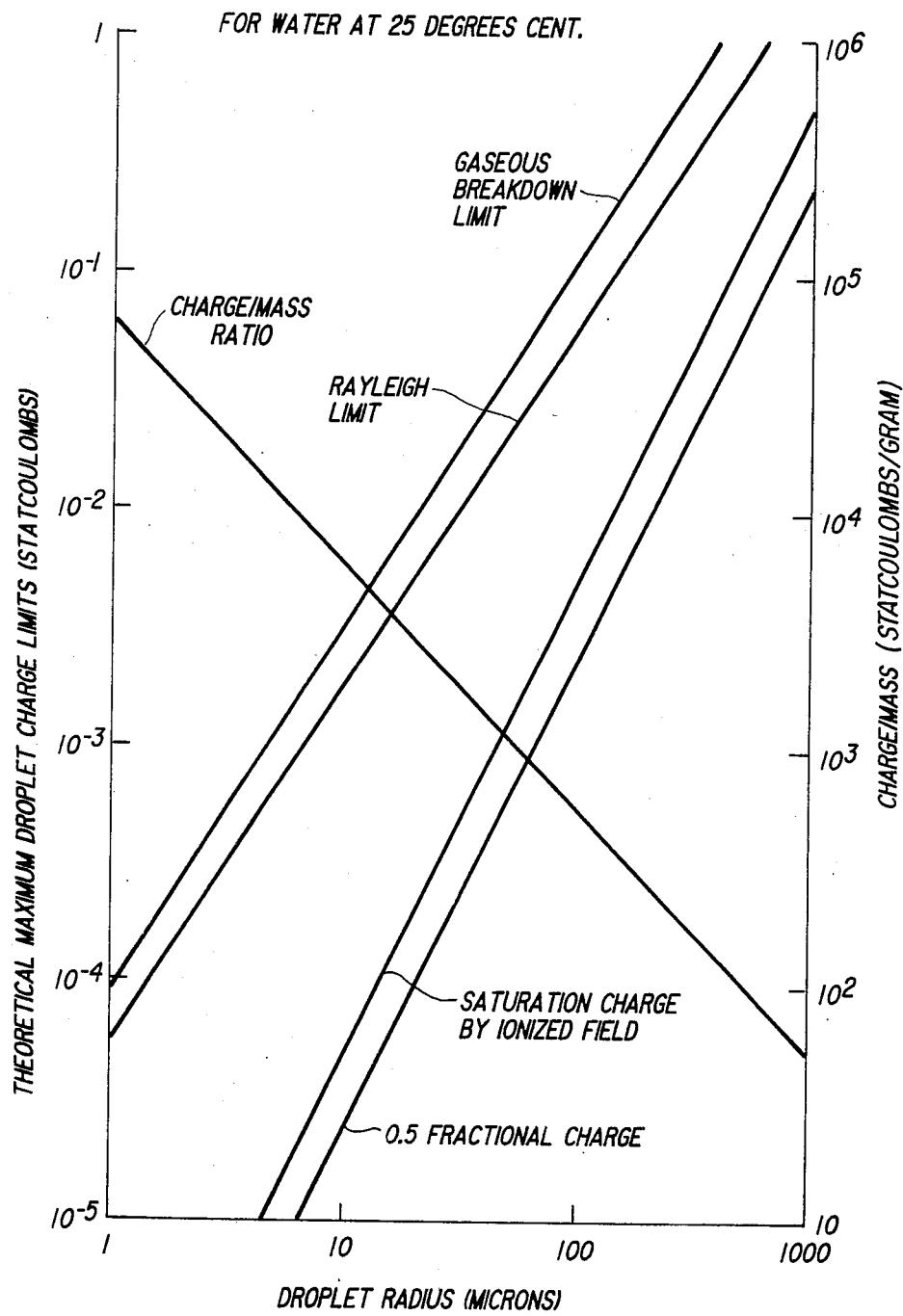
FIG. 2 is a graph showing the theoretical charge limits for water droplets at 25° C. in air as a function of radius.

Fortunately, it is both theoretically and technically possible to incorporate an additional particle deposition force into the ULV process. It is known that electrostatic forces—as opposed to volume-dependent gravitational, inertial and magnetic forces—act only on surface charge. Since surface area and volume very directly with particle diameter squared and cubed respectively, it is in the realm of finely divided particulate matter that electrostatic forces per unit volume or per unit mass of dispersed material attain useful magnitudes. The particle charge/mass ratio plotted in FIG. 2 as a function of droplet radius is technically attainable. This plotted curve also gives the electrical force/gravitational force ratio when each oridinate value is multiplied by the electrical/gravitational field field gradients at the location of the particle. The rapid increase of charge/mass ratio as droplet diameter decreases graphically illustrates the possible increase in total deposition force per gallon of ULV spray liquid which can be effected by charged particle technology. The following description of electrostatic precipitation serves as a background for the description of the invention which follows later.

The electrostatic precipitation process for argicultural sprays can be briefly discussed by considering its three distinct phases: particle charging, particle transit, and particle deposition.

Particle Charging: A relatively high net electrical charge of either desired sign can be readily imparted to individual agricultural particulates by several physical processes. Particle charging by ion attachment during passage through an ionized field created by a unipolar high-voltage corona discharge is a universally applicable method for use with solid or liquid particles provided they are dispersed in an airborne state at the time of charging. Ionized field particle charging is well developed mathematically in ionized-gas physics (5) and plasma physics (4). The net charge imparted to particles larger than approximately 0.5 microns diameter and throughout the ULV range is given by $$q_p = \left[1 + 2\frac{k-1}{k+2}\right] f 4\pi\epsilon_o E_o r_p^2 \quad (1)$$

where
$q_p$ = particle charge (coulombs)
$k$ = particle dielectric constant
$f$ = particle fractional charge
$\epsilon_o$ = permittivity of free space = $(8.85)(10)^{-12}$ col$^2$/nt m$^2$
$E_o$ = corona discharge field strength = $(5)(10)^5$ volts/m typical The particle fractional charge $f$ appearing in equation (1) attains a value of 0.5 saturation in one particle-charging time constant $t_o$ which is dependent mainly upon the ion concentration and mobility within the corona discharge. A fractional charge of 0.5 is typically achieved for a 2-millisecond particle-residence time in the ionized field. This is an often used and reasonable design value which is used in designing ULV spray charging systems.

The expression in brackets in equation (1) is a measure of the degree to which the corona charging flux lines are concentrated onto the particle. It ranges from 1.5 for a good dielectric such as transformer oil to a maximum value of 3 for conducting particles. Thus, particles composed of a solid or liquid dielectric material (such as many of the undiluted technical pesticide formulations) can be charged quite satisfactorily as compared to highly conductive metallic particles or water droplets.

For subsequent calculations the half-saturation droplet charge for water (dielectric constant $k=80$) is given approximately by the equation $$q_p = 6\pi\epsilon_o E_o r_p^2 \quad (2)$$

where particle charge is seen to be a function of radius squared. Experience has indicated that no difficulty should be encountered in ionized field charging of ULV-size droplets.

Law (10) investigated electrostatic induction as a means of charging pesticide sprays. Several induction charging electrodes which were developed which charged liquid droplets to the same degree as the ionized field method.

Law (11) has theoretically derived equations which establish upper bounds on the maximum droplet charge. The two physical phenomena which limit the maximum charge are hydrodynamic instability and gaseous breakdown of the air surrounding individual droplets. Values calculated from these theoretical equations are plotted in FIG. 2 as a function of droplet radius. Also shown are the saturation droplet charge ($f=1$) and the 0.5 fractional charge imparted to a water droplet in an ionized field.

Particle Transit and Deposition: Terminal velocity is a convenient index for comparing the relative effectiveness of the various force acting on an airborne particle in its transit to plant deposition surfaces. The terminal velocity of ULV-size droplets is given by Stokes' law. The simple form of this law, valid for the 3-100 micron diameter range, is $$V_t = \frac{F_p}{6\pi\eta r_p} \quad (3)$$

where
$V_t$ = particle terminal velocity (m/sec)
$F_p$ = resultant force acting on particle (nt)
$\eta$ = viscosity of air = $(1.81)(10)^{-5}$ (kg/m sec)

Figure 3:
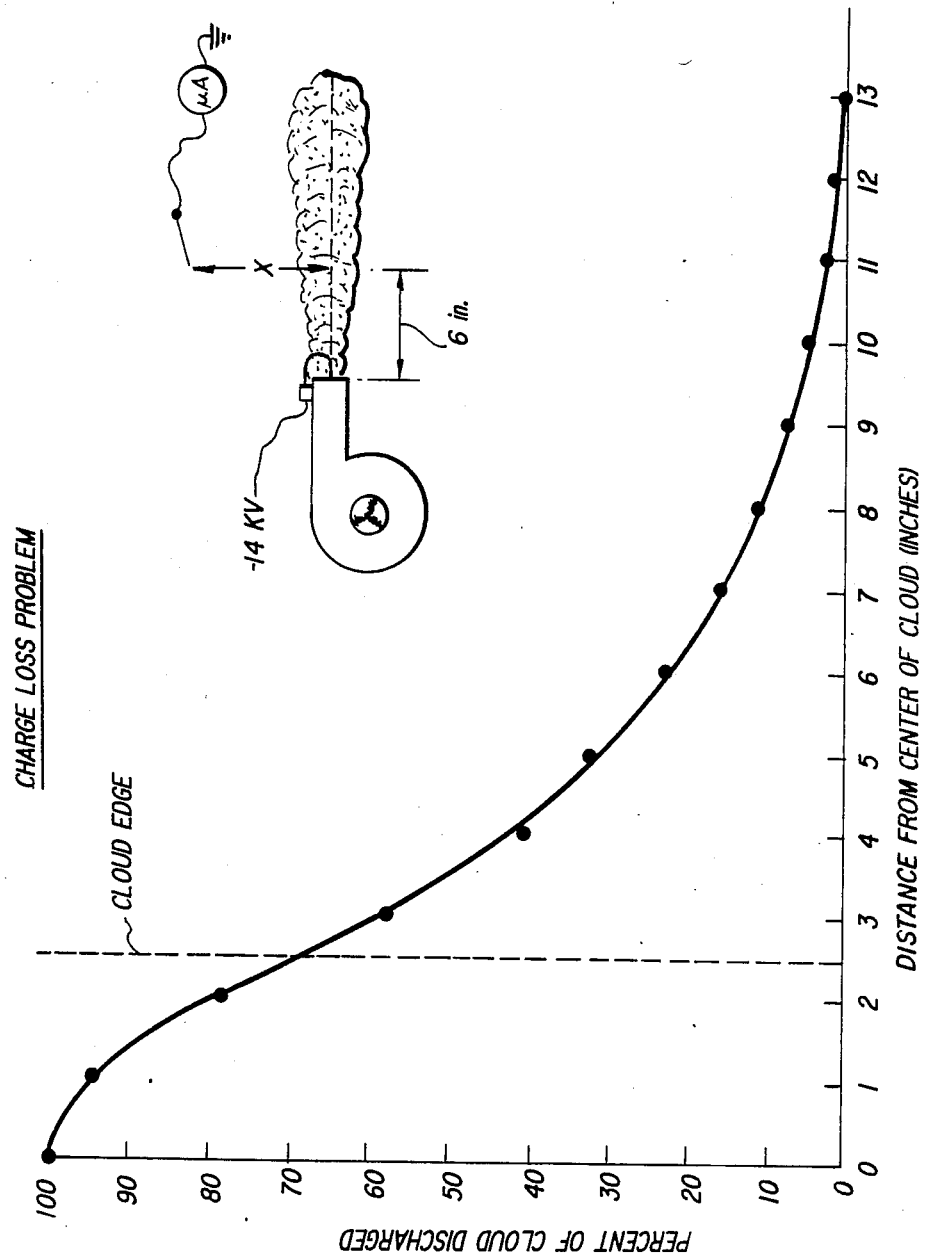
FIG. 3 is a graph showing the percentage of the total charge on a dust cloud discharged by a grounded point as a function of the distance from the cloud's center line.

Web (14) and Law (11) have established that gaseous discharge from charged airborne particulate clouds to grounded points is very active. Such discharge presently limits the electrostatic precipitation process drastically. FIG. 3 indicates how completely the cloud charge-loss can occur and at what distance it can be initiated.

The magnitude of the space charge density of the cloud is of paramount importance in initiating and sustaining the gaseous discharge. Electric space charge density is given as $$\rho_s = n_p q_p \quad (4)$$

where
$\rho_s$ = space charge density (coul/m$^3$)
$n_p$ = particle numerical density (No./m$^3$)

There is also an adverse effect which cloud breakdown as caused by excess space charge densities) has upon particle deposition onto plant surfaces (1). Particle resistivity is known to enter the breakdown process.

The objectives of the following mathematical analysis, which is useful for understanding control of the ULV-electrostatic dual-particle-size process, are to theoretically determine what effects the reduced application reates are reduced droplet diameters associated with ULV pesticide application have on (a) the electric space charge density of the particulate cloud and (b) the terminal velocity components acting on a single particle as caused by gravitational force, applied electric field force, electrostatic image force, and the force due to the space-charge electric field.

An approximation of the average space charge density within and surrounding the crop canopy can be calculated as a function of liquid application rate per acre $V_L$ and droplet radius $r_p$. A typical row crop of 40 inch height has an application volume $V_a$ of 1 acremeter or 4047 m$^3$. The average space charge density becomes $$\rho_s = n_p q_p \quad (4)$$

$$\rho_s = \frac{V_L q_p}{V_p V_a} \quad (5)$$

For spherical particles of volume $V_p$ this becomes $$\rho_s = \frac{V_L q_p}{\frac{4}{3}\pi r_p^3 V_a} \quad (6)$$

For water spray droplets charged to 0.5 saturation in an ionized field, this becomes $$\rho_s = \frac{6\pi\epsilon_o E_o r_p^2 V_L}{\frac{4}{3}\pi r_p^3 V_a} \quad (7)$$

which simplifies to give $$\rho_s = \frac{9\epsilon_o E_o}{2V_a} \frac{V_L}{r_p} \quad (8)$$

Figure 4:
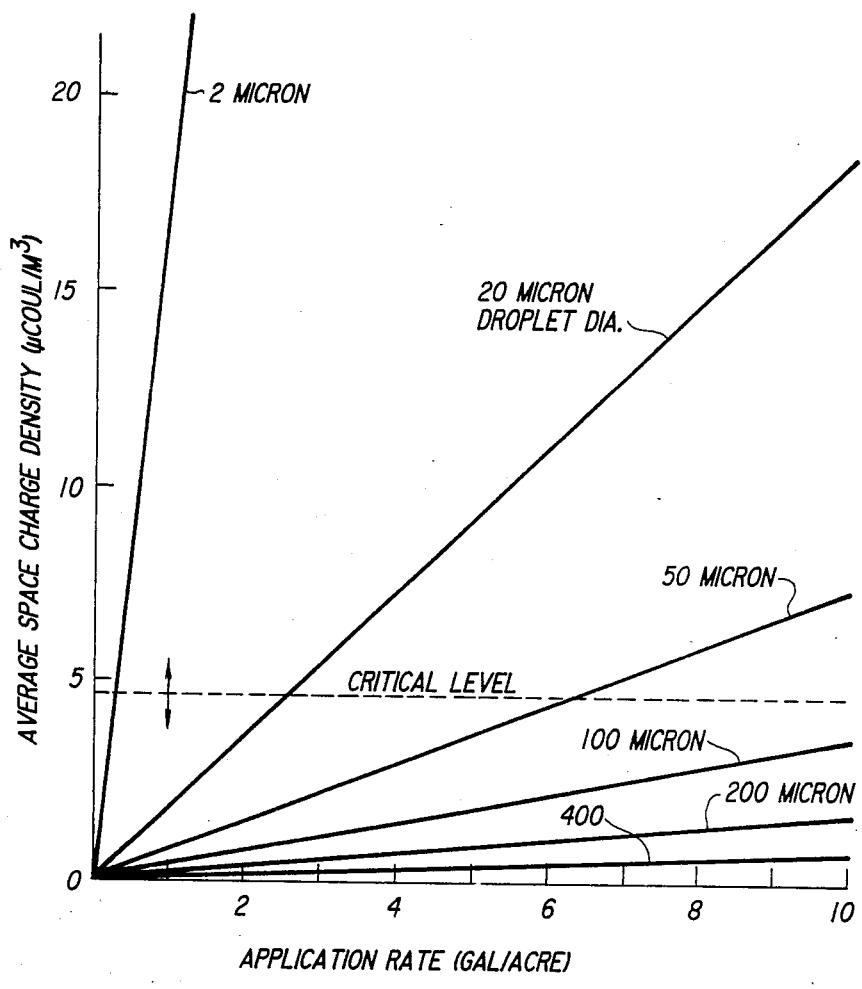
FIG. 4 is a graph showing the average space charge density in the region of a plant as a function of application rate and particle droplet diameter.
Figure 5:
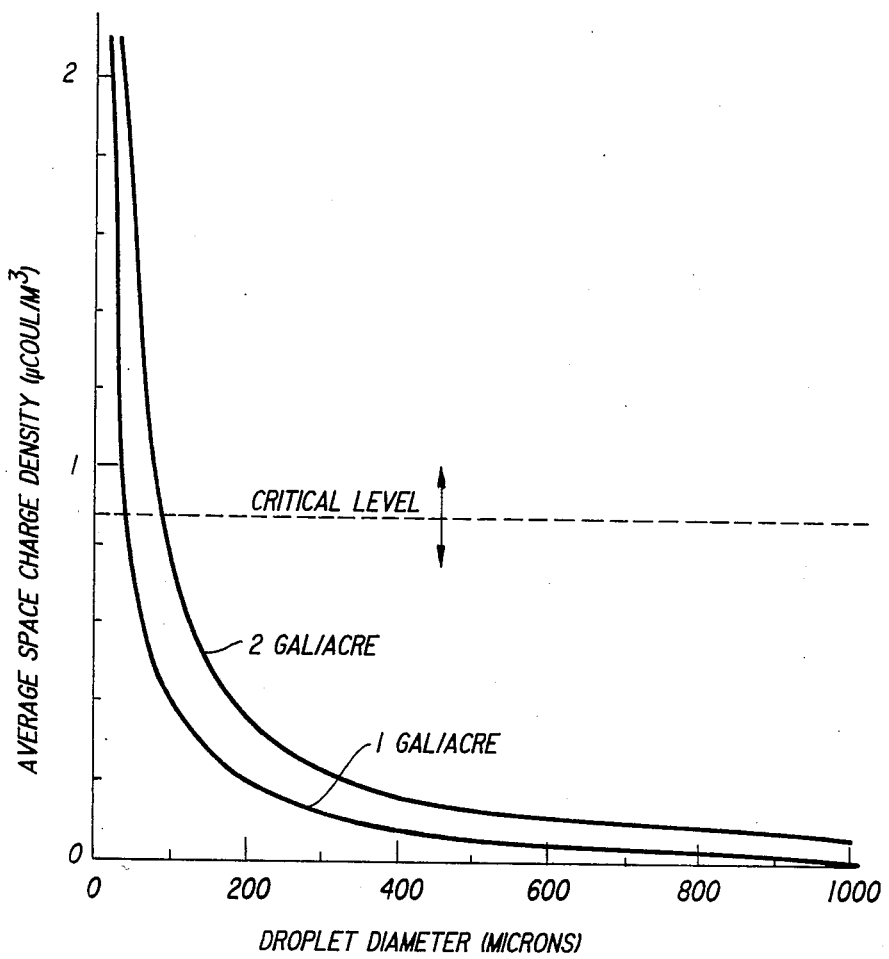
FIG. 5 is a graph showing the average space charge density in a plant region as a function of droplet diameter for different application rates.

Equation (8) indicates that the average space charge varies as the first power directly with application rate and inversely with particle radius. Numerical values of the average space charge density in the plant vicinity are plotted as a function of application rate $V_L$ (gallons-/acre) with droplet diameter as a parameter in FIG. 4. FIG. 5 illustrates the rapid increase in space charge density caused by more finely atomizing a given gallonage of spray liquid. The rate of change is particularly great in the ULV droplet size region under 100 microns diameter. A horizontal line is shown in FIGS. 4 and 5 placed at some arbitrary value of space charge. This is intended to indicate the existence of critical space charge density value above which an unacceptable degree of cloud discharge occurs. This critical value will depend upon ambient air ion content, plant type and spacing, particle resistivity, and relative humidty. It is seen on FIG. 5 that in the ULV range, a slight shift in atomization characteristics caused a large shift in space charge relative to the critical value. Shifts in gallon-/acre are of much less concern in this regard.

Figure 6:
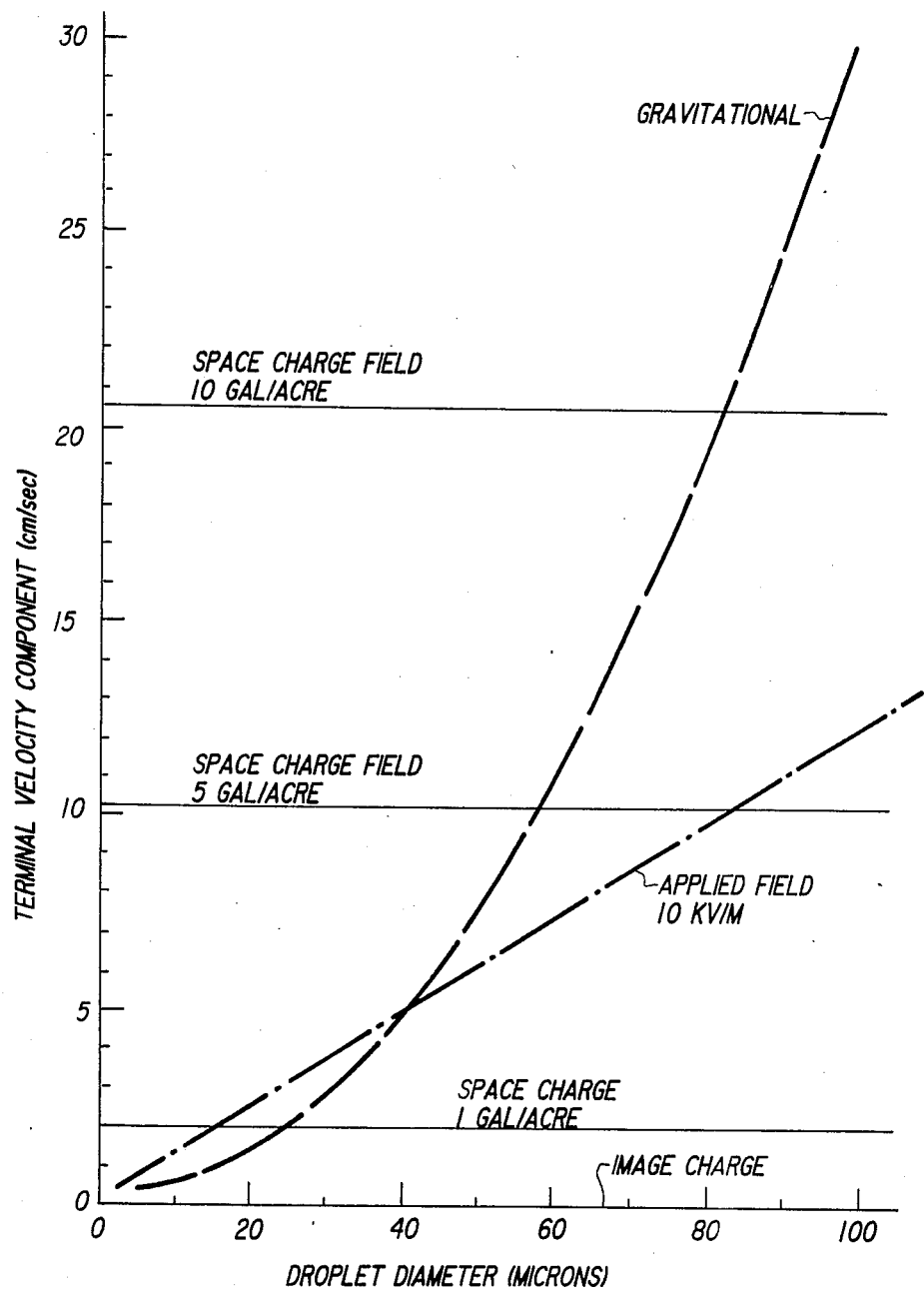
FIG. 6 is a graph showing the terminal velocity components due to the various force fields acting on a charged airborne water droplet.
Figure 7:
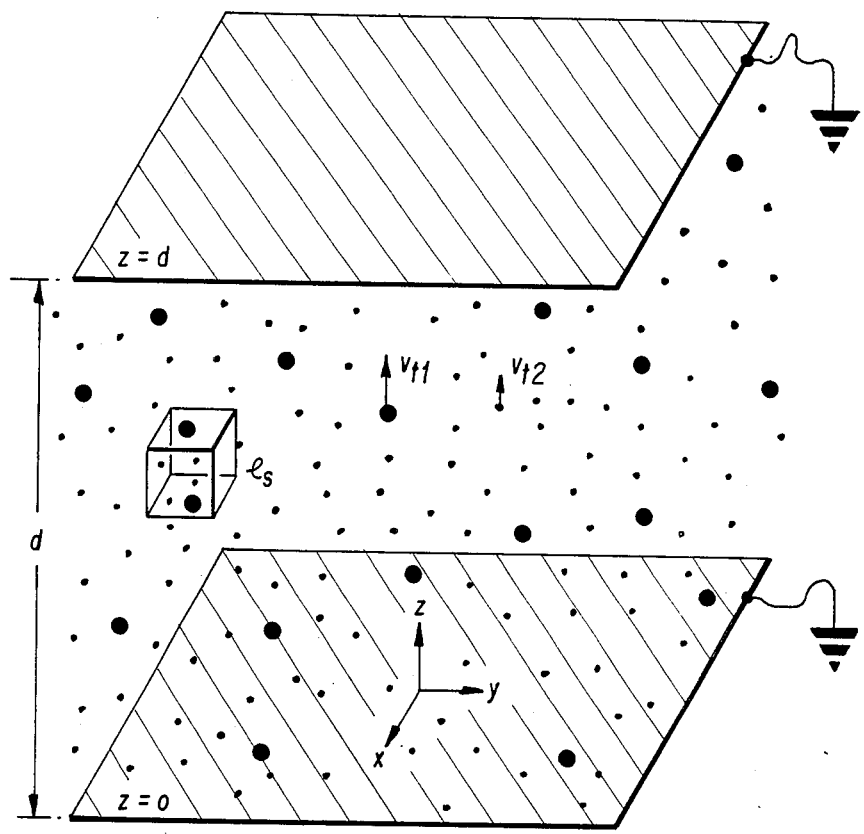
FIG. 7 is a graph of the dual particle-species model for space-charge deposition described in this specification.

The components of the terminal velocity of an airborne droplet in transit toward a deposit surface may be calculated for ULV droplet sizes if the mathematical expressions for the appropriate particle forces $F_p$ in equation (3) are known. The magnitudes of these terminal velocities are calculated below as a function of droplet diameter and gallons/acre for operational conditions expected to be typical. The results of these theoretical calculations are presented in Table 1 and FIG. 6 for droplet diameters of interest in the ULV techique. Expressions of the functional dependence of terminal velocity upon droplet size and application rate follow.

TABLE 1

Terminal Velocity Components for Various Forces Active on Airborne Pesticide Droplets (m/sec)*

| Droplet Radius (microns) | Gravitational Field | Applied Electric Field | Electro-Static Image | Space Charge Field |
|---|---|---|---|---|
| 1 | 1.20 × 10$^{-4}$ | 2.44 × 10$^{-3}$ | 4.58 × 10$^{-10}$ | 2.06 × 10$^{-2}$ |
| 10 | 1.20 × 10$^{-2}$ | 2.44 × 10$^{-2}$ | 4.58 × 10$^{-7}$ | ↓ |
| 20 | 4.80 × 10$^{-2}$ | 4.89 × 10$^{-2}$ | 3.66 × 10$^{-6}$ | ↓ |
| 25 | 7.50 × 10$^{-2}$ | 6.10 × 10$^{-2}$ | 7.15 × 10$^{-6}$ | ↓ |
| 30 | 1.08 × 10$^{-1}$ | 7.35 × 10$^{-2}$ | 1.24 × 10$^{-5}$ | ↓ |
| 40 | 1.92 × 10$^{-1}$ | 9.80 × 10$^{-2}$ | 2.93 × 10$^{-5}$ | ↓ |
| 50 | 3.00 × 10$^{-1}$ | 1.22 × 10$^{-1}$ | 5.73 × 10$^{-5}$ | ↓ |
| 100 | 1.20 | 2.44 × 10$^{-1}$ | 4.58 × 10$^{-4}$ | ↓ |
| 200 | 4.80 | 4.89 × 10$^{-1}$ | 3.67 × 10$^{-3}$ | ↓ |
| 400 | 19.2 | 1.95 | 2.94 × 10$^{-2}$ | ↓ |
| 500 | 30.0 | 1.22 | 5.73 × 10$^{-2}$ | ↓ |

*For water droplets at 0.5 saturation charge applied at a rate of 1 gal/acre.

Gravitational Force—The terminal velocity attained by a water droplet accelerated by gravity is given as $$F_p = m_p g \quad (9)$$

$$F_p = \frac{4}{3}\pi r_p^3 \rho_L g \quad (10)$$

$$V_t = \frac{2\rho_L g}{9\eta} r_p^2 \quad (11)$$

where
$\rho_L$ = liquid mass density = 10$^3$ kg/m$^3$ for H$_2$O
g = gravitational acceleration = 9.81 m/sec$^2$ Applied Electric Field Force—An externally applied driving field force can fairly easily be established by maintaining a high D.C. voltage on a large metal plate positioned above the plant tops. Water droplets charged to 0.5 fractional charge and released within this applied field $E_a$ are driven toward the top leaves of the grounded plants at a velocity given by $$F_p = q_p E_a \quad (12)$$

$$F_p = 6\pi\epsilon_o E_o r_p^2 E_a \quad (13)$$

$$V_t = \frac{\epsilon_o E_o E_a}{\eta} r_p \quad (14)$$

It is practical to maintain a 10 kilovolt/meter driving field by applying 5 kilovolts to a plate about 20 inches (0.5 m) above the plant tops. Terminal velocity values calculated by equation (14) with $E_a = 10$ kv/m are listed in Table 1 and plotted in FIG. 6.

Electrostatic Image Force—A charge droplet located near a grounded plant surface is attracted by an induced image charge of opposite sign within the leaf. The force of attraction for a droplet-to-leaf spacing d' is given for a water droplet at 0.5 fractional charge as $$F_p = \frac{q_p^2}{4\pi\epsilon_o(2d')^2} \quad (15)$$

$$F_p = \frac{9\pi\epsilon_o E_o^2}{4(d')^2} r_p^4 \quad (16)$$

$$V_t = \frac{3\epsilon_o E_o^2}{8\eta(d')^2} r_p^3 \quad (17)$$

Values are calculated from equation (17) for a droplet located 1 cm from the leaf surface.

Space-Charge Field Force—The movement of a charged droplet within the plant canopy is dependent upon the electric field produced by the space charge within the canopy. An approximate mathematical model is provided by considering a charged droplet (f=0.5) immersed within a space charge of density $\rho_s$ uniformly sandwiched between two infinite parallel conducting plates at ground potential. The parallel plates, which simulate plant leaves, are located in the X-Y plane at Z=0 and at Z=d while the droplet considered is located between the plates at a distance Z. An equation for this field configuration has been developed (2) and is given aso $$E_s = \frac{\rho_s Z}{\epsilon_o} - \frac{\rho_s d}{2\epsilon_o} \quad (18)$$

$$F_p = q_p E \rho_s \quad (19)$$

$$F_p = 6\pi\epsilon_o E_o r_p^2 \frac{\rho_s Z}{\epsilon_o} - \frac{\rho_s d}{2\epsilon_o} \quad (20)$$

Using equation (8) for the average space charge density, this becomes $$F_p = \frac{27\pi\epsilon_o E_o^2 \left(Z - \frac{d}{2}\right)}{V_a} V_L r_p \quad (21)$$

$$V_t = \frac{9\epsilon_o E_o^2 \left(Z - \frac{d}{2}\right)}{2V_a \eta} V_L \quad (22)$$

Terminal velocity values are calculated by equation (22) for a particle situated at Z=1 cm. from the surface of leaves which are spaced at a separation distance d=10 cm. and for an application rate of $V_L = 1$ gallon/acre. Results are given in Table 1 and FIG. 6.

Note that this is the only case in which the terminal velocity is dependent upon liquid application rate $V_L$ and independent of particle radius $r_p$.

The preceding mathematical evaluation shows some of the problems involved in electrostatic application of particles to plant surfaces in agricultural spraying operations. Although the present invention has applications in other areas, the invention was initially designed to overcome these problems.

Two phenomena exist which presently limit the deposition of charged pesticide particles as driven by their own space-charge field:

(a) The time-dependent space-charge driving field decays as the pesticide cloud deposits. As a result, a very appreciable portion of the final airborne pesticide cloud experiences only marginal increases in particle terminal velocity due to the space-charge field effect. (Of course, electrostatic image forces are active even on the final airborne particles.)

(b) The electrical charge imparted to individual pesticide particles must remain sufficiently low to assure that no gaseous discharge of the cloud occurs due to an excess space-charge field generated by the charged particles themselves. This space-charge field is a linear function of the individual particle charge $q_p$ as seen by equations (4) and (18). Since the electrical driving force active on an individual pesticide particle is given by equation (19) as the product of the particle charge $q_p$ times the space-charge field, the terminal velocity achieved by the interaction of the space-charge field with any given size pesticide particle depends upon the square of the individual particle charge $q_p$. For instance, if the charge imparted to airborne particles is halved in order to remain under some critical space-charge field intensity which would cause breakdown, then the terminal velocity of individual pesticide particles is reduced to $\frac{1}{4}$.

The following is a theoretical analysis of the present invention, a new concept in electrostatic precipitation of pesticides which may greatly reduce these two limiting phenomena discussed above. Significant enhancement of the space-charge deposition of pesticide particles within the plant canopy should result.

The concept involves the uniform dispersion of two distinct species of charged airborne particles within the plant canopy—a toxic species and an inert species—and is based upon the following principles of charged particulate technology:

(a) The electric mobility of an airborne particle charged by the ionized field process is a linear function of particle radius $r_p$.

(b) The resultant space-charge field which exists within a region is due to the superposition of the fields generated by all species of charged airborne particles within the region.

(c) The charge/mass ratio varies inversely with radius $r_p$ for particles charged by the ionized field process.

(d) The fraction of saturation charge which a particle attains in the ionized field charging process is independent of particle radius $r_p$.

Figure 8:
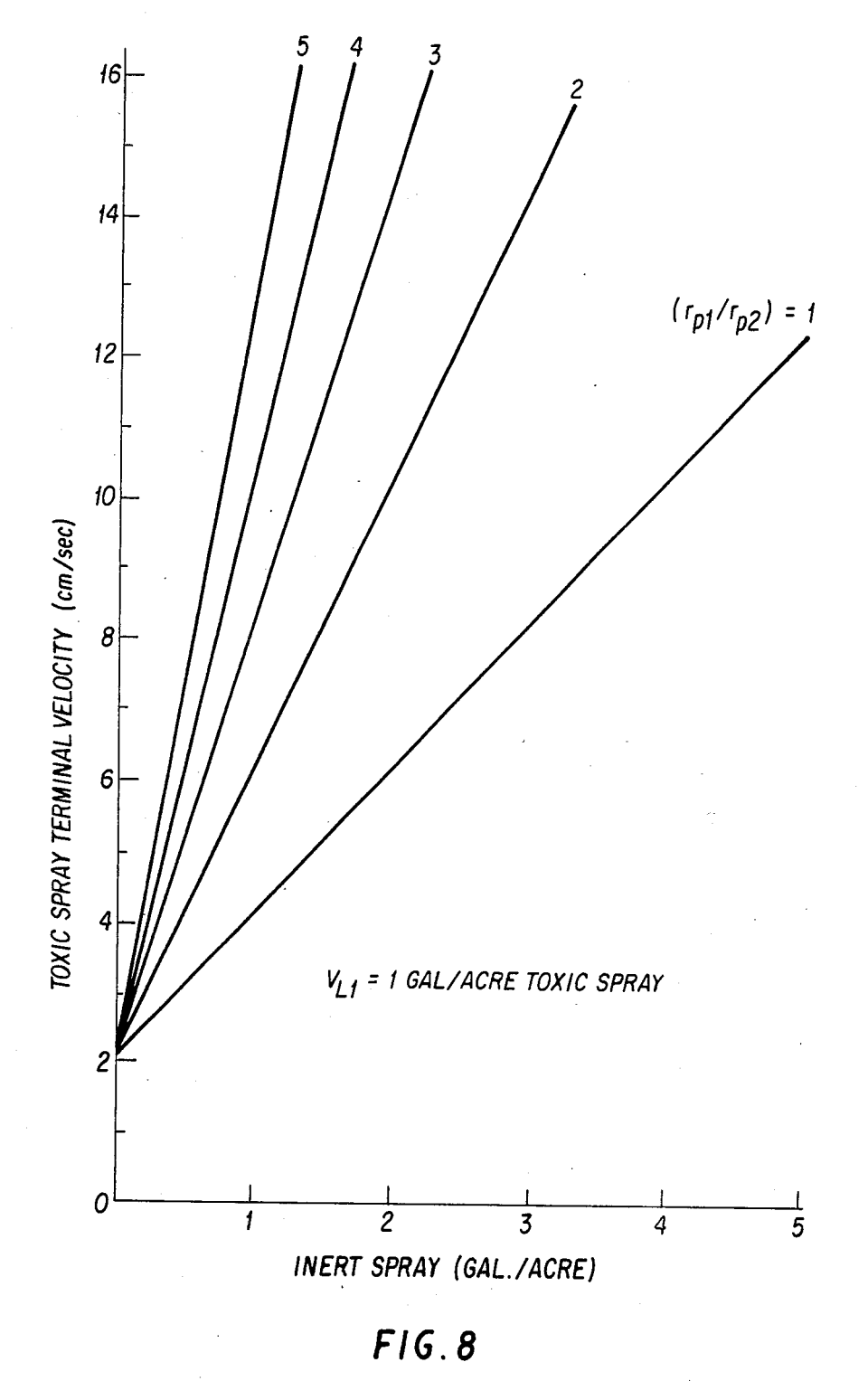

Dual Particle—Specie Model—A better understanding of the present invention can be obtained by consideration of the model shown in FIG. 8 which depicts two particle species (#1 and #2) which have been charged in the same ionized field charging device and uniformly dispersed between grounded leaf surfaces. The toxic specie #1 and the inert specie #2 have particle radii $r_{p1}$ and $r_{p2}$ and have been applied at rates $V_{L1}$ and $V_{L2}$, respectively. The total space charge density is given by equation (8) as $$\rho_s = \left(\frac{9\epsilon_o E_o}{2V_a}\right)\left(\frac{V_{L1}}{r_{p1}} + \frac{V_{L2}}{r_{p2}}\right) \tag{23}$$

The resultant space-charge field from equations (18) and (23) becomes $$E_{p2} = \left(\frac{9E_o}{2V_a}\right)\left(\frac{V_{L1}}{r_{p1}} + \frac{V_{L2}}{r_{p2}}\right)\left(Z - \frac{d}{2}\right) \tag{24}$$

The terminal velocities which particles of either specie attain when driven by this combined field is given as $$V_t = k_p E_{ps} \tag{25}$$

where $k_p$=electrical mobility of charged particulate $$\left(\frac{m^2}{\text{volts sec}}\right) \tag{26}$$

$$k_p = \frac{q_p}{6\pi\eta r_p}$$

For aqueous-base droplets charged to f=0.5 fractional charge this mobility expression becomes approximately $$k_p = \left(\frac{\epsilon_o E_o}{\eta}\right) r_p \tag{27}$$

Thus, the terminal velocity $v_{t1}$ at which the toxic particles (#1) are driven towards the leaf surfaces is given by the product of equations (24) and (27) as $$V_{t1} = \left(\frac{9\epsilon_o E_o^2}{2V_a\eta}\right)\left(Z - \frac{d}{2}\right)\left(V_{L1} + V_{L2}\left(\frac{r_{p1}}{r_{p2}}\right)\right) \tag{28}$$

It is seen that for a single specie particle, equation (28) reduces as it should to equation (22) in which terminal velocity is independent of particle size. However, when an inert particles specie (#2) is present, the terminal velocity of the toxic specie is enhanced to a degree dependent both upon the application rate $V_{L2}$ of the inert material as well as upon the ratio $(r_{p1}/r_{p2})$ of the particle radii.

FIG. 8 illustrates graphically the theoretical increase in pesticide terminal velocity to be expected in the absence of breakdown. As an example, the terminal velocity of pesticide particles within the plant canopy is enhanced by a factor of 6 when the toxic particles are accompanied by an equal application volume of inert material which has 1/5 the diameter of the toxic particles.

Operational Constraints—A limitation on space-charge deposition of pesticide particles caused by the decay of the self-driving field was mentioned earlier. By imposing two judicious constraints on the mathematical model (equation 28) of the dual-specie space-charge system, the deposition of practically all of the toxic particles can be assured prior to any great decay of the driving field. Two such constraints for preferential deposition of specie #1 are:

(a) At least 80% of the initial space-charge field should be generated by the inert specie (#2). From equation (8) this condition occurs for $$s2 \geq 4\,s1 \tag{29}$$

$$\left(\frac{V_{L2}}{r_{p2}}\right) \geq 4\left(\frac{V_{L1}}{r_{p1}}\right) \tag{30}$$

(b) The electric mobility of the toxic specie (#1) should be at least 5 times as great as that of the inert specie. This constraint eliminates the use of highly mobile air ions as the inert specie. From equation (27) this becomes $$K_{p1} \geq 5k_{p2} \tag{31}$$

$$r_{p1} \geq 5r_{p2} \tag{32}$$

Using equation (32) the equation (30) reduces to $$\left(\frac{V_{L2}}{V_{L1}}\right) \geq 0.8 \tag{33}$$

Thus, roughly 64% of the initial space charge field will still exist when the final toxic particle has been deposited if (a) at least 80% as much volume of inert species is dispersed along with the active species, and (b) the active species particle diameter is at least 5 times as large as the inert partices. Poor deposition of the remaining inert particles due to further field decay should be of neither economic nor ecological consequence.

Field-Breakdown Control—The degree of enhancement permitted in toxic particle terminal velocity and in field decay conditions analyzed above will still be dictated by the limitations imposed on total space charge density by the field-breakdown problem. The total space charge density should still be monitored and maintained at less than the critical breakdown value. The dual particle-species concept theoretically offers several methods of maintaining the toxic specie terminal velocity at a high value (as compared with a single-species system) while operating under any specified critical value for breakdown. It has been shown for a single-species system that the particle terminal velocity decreases with $q_p^2$ while the space charge field falls off only linearly with $q_p$ when precautions against breakdown are implemented. With the dual-specie concept it will be possible to maintain the toxic particle charge $q_{p1}$ constant at a high fraction of saturation (say f=0.5) while controlling the space charge field at just less than breakdown by varying one and/or the other of the following inert-material parameters:

(a) The application rate $V_{L2}$—to be consistent with prior constraints, preferably keep $V_{L2} \geq 0.8V_{L1}$. However, $V_{L2} \geq 0.4V_{L1}$ also is suitable.

(b) The radius $r_{p2}$—the mobility constraint dictates that desirably $r_{p2} \leq 0.2\,r_{p1}$. However, $0.5r_{p2} \leq r_{p1}$ also is suitable. For the relatively low ULV flow rates, magnetostrictive or piezoelectric atomization devices are practical. These devices can provide rapid and fairly accurate droplet-size control and, hence, space charge control. Recall from FIG. 5 the extremely large shift in space charge density caused by droplet size changes at a fixed flow rate.

(c) The fractional charge $f_2$—this control technique would require separate particle charging devices for the inert and the toxic species.

Techniques for controlling these parameters are well known and are described, for example, in the patents cited in the section of the specification entitled "Background of the Invention".

Although this invention arose as a result of consideration of agricultural spraying operations, it is also useful in other types of industrial spraying operations such as painting of metal surfaces and other types of coating operations that are currently carried out electrostatic deposition techniques. For example, in a painting operation, the active material as described herein would comprise a paint. Since very little of the inert material is deposited on the surface being coated, the paint would be at or near its optimum concentration. The inert material under these circumstances would be a paint thinner or other compatible material.

The process can also be applied to the removal of particulate material from a gas stream, such as an electrostatic smoke stack scrubber. By introducing a stream of small inert particles, such as charged water particles, higher terminal velocities (and thus higher removal rates) can be obtained. Thus, smaller collector plates or other collecting surfaces and/or greater removal efficiencies can be obtained in electrostatic particle precipitators.

The terms "active" and "inert" are used herein to distinguish the two particles without regard to a specific activity since the invention does not depend on the material being sprayed or its activity. The "active" material is the one which is desired to be deposited on the target surface while the "inert" material is a charge carrier. The inert material (being finer and more subject to drift) is preferably environmentally inert and is commonly merely water.

As has been pointed out previously, the present invention also does not rely on the use of any particular apparatus to carry out the invention. For example, the invention can be readily carried out by using two different nozzles to produce liquid particles of different sizes which are mixed in the same spatial volume. Alternatively, a smoke-generating apparatus (which typically operate by dropping oil onto a hot plate) can be used to produce the small inert particles into which a dispersion of larger particles is inserted. Either liquid or solid particles can be used for both the inert and the active particles. Water and smoke are preferred inert particles for agricultural applications.

EXAMPLE

The principles involved in this invention were demonstrated in a simple experiment. Apple surfaces were used as targets and examined microscopically for coverage. Two sizes of inert particles were used: small particles of 1-3 micron diameter and large particles of 40-150 micron diameter (obtained from a 325 mesh screen). The particles were sprayed with air using an operating pressure of 100 psi and a flow rate of 100 cfm. An ionizing field of 10kV was used to produce a negative charge in each of four treatments, each of which used equal total weights of particles: (1) fine particles alone, (2) coarse particles alone, (3) 1:1 ratio of fine to coarse particles, and (4) 2:1 ratio of fine to coarse particles.

When coarse dust alone was used (trial 2) there was no visible current in the dust stream. When fine particles alone were used (trial 1), there was a 3-4 microamp current. Better surface coverage by large particles was obtained in trial 4 (2:1 weight ratio) than in trial 2 using only large particles. Using only half as many large particles in treatment 3, an equal coverage of large particles on the surface was detected when compared to trial 2. Although these results were not quantitative, they demonstrate the improved coverage obtained when using the dual particle sizes of the invention.

REFERENCES

The following publications, which are cited in this specification, demonstrate the level of skill of those skilled in the art to which this invention pertains. Each publication in this list as well as all other patents and publications mentioned in this specification are herein incorporated by reference in the location where each individual publication or patent is cited.

1. Bowen, H. D. and Splinter, W. F. 1968. Field testing of improved electrostatic dusting and spraying equipment. ASAE Paper No. 68-150, ASAE, St. Joseph, Mich.
2. Bowen, H. D., Splinter, W. E. and Carleton, W. M. 1964. Theoretical implications of electric fields on deposition of charged particles. Trans. of the ASAE 7:(1)75-82.
3. Brooks, F. A. 1947. The drifting of poisonous dusts applied by airplanes and ground rigs. Agricultural Engineering. 28:233-239.
4. Brown, S. C. 1959. Basic data of plasma physics. John Wiley & Sons, New York.
5. Cobine, J. D. 1958 Gaseous conductors: theory and engineering applications. Dover Publications, Inc. New York.
6. Ennis, W. B., Jr. and Williamson, R. E. 1963. Influence of droplet size on effectiveness of low-volume herbicidal sprays. Weeds. 11:67-72.
7. Himel, C. H. and Moore, A. D. 1967. Spruce budworm mortality as a function of aerial spray droplet size. Science (Washington) 156:1250-1.
8. Himel, C. H. 1969. The optimum size for insecticide spray droplets. Journal Econ. Entomolo. 62:919-25.
9. Himel, C. H., Keathley, J. P. and Miller, M. C. 1971. The case for finely atomized sprays for maximum efficiency in insect control. ASAE Paper No. 71-660, ASAE, St. Joseph, Mich.
10. Law, S. E. 1966. Charging liquid spray by electrostatic induction. Trans. of the ASAE 9:(4)501-506.
11. Law, S. E. 1968. Charge loss phenomena active on liquid droplets. Unpublished Ph.D. thesis, Department of Biological and Agricultural Engineering, North Carolina State University, Raleigh.
12. Roberts, R. B., Lyon, R. L., Page, M. and Miskus, R. P. 1971. Laser holography: its application to the study of the behavior of insecticide particles. Journal of Econ. Entomolo. 64:(2)533-536.
13. Threadgill, E. D. and Smith, D. B. 1971. Effects of physical and meteorological parameters on the drift on controlled size ULV droplets. ASAE Paper No. 71-663, ASAE, St. Joseph, Michigan.
14. Webb, B. K. 1966. Electric field breakdown phenomena in the application of charged dust. Unpublished Ph.D. thesis, Department of Biological and Agricultural Engineering, North Carolina State University, Raleigh.

Obviously numerous additional modifications and variations of the present invention are possible in light of the above teachings. It is therefore to be understood that within the scope of the appended claims the invention may be practiced otherwise than as specifically described herein.

What is claimed as new and desired to be secured by Letters Patent of the United States is:

1. A method for increasing the efficiency of electrostatic deposition of particulate matter on a surface, which comprises:

preparing a dispersion of electrostatically charged particles of an active material to be deposited on said surface, wherein said particles of active material have an average radius of $r_{p1}$ and a total volume of $V_{L1}$, in a space adjacent to said surface which contains a dispersion of particles of an inert material, electrostatically charged with the same polarity as said particles of active material, wherein said particles of inert material have an average radius of $r_{p2}$ and a total volume of $V_{L2}$, wherein $r_{p1} > r_{p2}$ and $$\frac{V_{L2}}{V_{L1}} \geqq 0.2.$$

2. The method of claim 1, wherein $r_{p1} \geqq 2r_{p2}$.

3. The method of claim 1, wherein $r_{p1} \geqq 5r_{p2}$.

4. The method of claim 3, wherein $$\frac{V_{L2}}{V_{L1}} \geqq 0.8.$$

5. The method of claim 1, wherein $$\frac{V_{L2}}{V_{L1}} \geqq 0.4.$$

6. The method of claim 1, wherein $$\frac{V_{L2}}{V_{L1}} \geqq 0.8.$$

7. The method of claim 6, wherein $r_{p1} \geqq 5r_{p2}$.

8. The method of claim 1, wherein the active material comprises a paint.

9. The method of claim 8, wherein the inert material comprises a paint thinner.

10. The method of claim 1, wherein the active material is a particulate impurity in a gaseous stream and said surface is an impurity collecting area.

11. The method of claim 1, wherein the active material is a pesticide or herbicide and said surface is a plant surface.

* * * * *